US00PP22136P2

(12) United States Plant Patent
Davidson

(10) Patent No.: US PP22,136 P2
(45) Date of Patent: Sep. 6, 2011

(54) ***MONARDA* PLANT NAMED 'MCMUM'**

(50) Latin Name: *Monarda didyma*
Varietal Denomination: MCmum

(75) Inventor: Campbell G. Davidson, Swift Current (CA)

(73) Assignee: Her Majesty the Queen in right of Canada, as represented by the Minister of Agricultural and Agrifoods, Lacombe (CA)

( * ) Notice: Subject to any disclaimer, the term of this patent is extended or adjusted under 35 U.S.C. 154(b) by 0 days.

(21) Appl. No.: 12/800,939

(22) Filed: May 26, 2010

(51) Int. Cl.
*A01H 5/00* (2006.01)

(52) U.S. Cl. ..... Plt./455

(58) Field of Classification Search ..... Plt./455
See application file for complete search history.

*Primary Examiner* — Kent L Bell
(74) *Attorney, Agent, or Firm* — Penny J. Aguirre

(57) ABSTRACT

A new cultivar of *Monarda didyma* named 'MCmum' characterized by its large pink inflorescences that are present abundantly from July to early September, its compact, mounded plant habit, its medium size, its hardiness in U.S.D.A. Zones 3 to 8, and its dark green foliage that has shown resistance to powdery mildew.

2 Drawing Sheets

Botanical classification: *Monarda didyma.*
Variety denomination: 'MCmum'.

BACKGROUND OF THE INVENTION

The present invention relates to a new and distinct cultivar of *Monarda didyma*. The new cultivar will be referred to hereafter by its cultivar name, 'MCmum'. 'MCmum' is a new variety of bee balm suitable for landscape plantings.

The new cultivar of *Monarda* was a selection from an on going breeding program by the Inventor in Morden, Manitoba, Canada. The Inventor allowed open pollination to occur between specific unnamed plants in his breeding line and pooled all the resulting seed from his crosses and evaluated the resulting seedlings based on the objectives of the breeding program. The specific parents are unknown. The Inventor selected 'MCmum' as a single unique plant in summer of 2007.

The new cultivar was first asexually propagated by the Inventor by stem cuttings in Morden, Manitoba, Canada in 2008. Asexual propagation in Morden, Manitoba, Canada and St. Paul, Minn. has determined that the characteristics of this cultivar are stable and are reproduced true to type in successive generations.

SUMMARY OF THE INVENTION

The following traits have been repeatedly observed and represent the characteristics of the new *Monarda* as observed for a period of three years in Morden, Manitoba, Canada and St. Paul, Minn. These attributes in combination distinguish 'MCmum' as a unique cultivar of *Monarda.*

1. 'MCmum' exhibits large pink inflorescences with high flower count.
2. 'MCmum' blooms abundantly from July to early September.
3. 'MCmum' exhibits dark green foliage.
4. 'MCmum' exhibits a mid-sized, compact and mounded habit.

5. 'MCmum' has shown good resistance to powdery mildew (*Sphaerotheca pannosa* var. *rosa*) under the conditions tested.
6. 'MCmum' is hardy in U.S.D.A. Zones 3 to 8.

The new cultivar of *Monarda* can be readily distinguished from other cultivars. 'Petite Delight' (U.S. Plant Pat. No. 10,784), 'AChall' (U.S. Plant Pat. No. 19,582) and 'ACrade' (U.S. Plant Pat. No. 19,580) are the closest comparison cultivars known to the Inventor. *Monarda* 'Petite Delight' differs from 'MCmum' in having larger, purple-violet inflorescences and a smaller plant size. 'AChall' differs from 'MCmum' in having larger, fuschia-purple inflorescences, an upright habit, and a smaller size. 'ACrade' differs from 'MCmum' in having purple-violet inflorescences and a smaller plant size.

BRIEF DESCRIPTION OF THE DRAWING

The accompanying colored photographs illustrate the overall appearance and distinct characteristics of the new *Monarda*, 'MCmum', as grown outdoors in a trial plots in Morden, Manitoba, Canada. The plants were approximately three years in age and the photographs were taken in mid summer.

Figure 1:
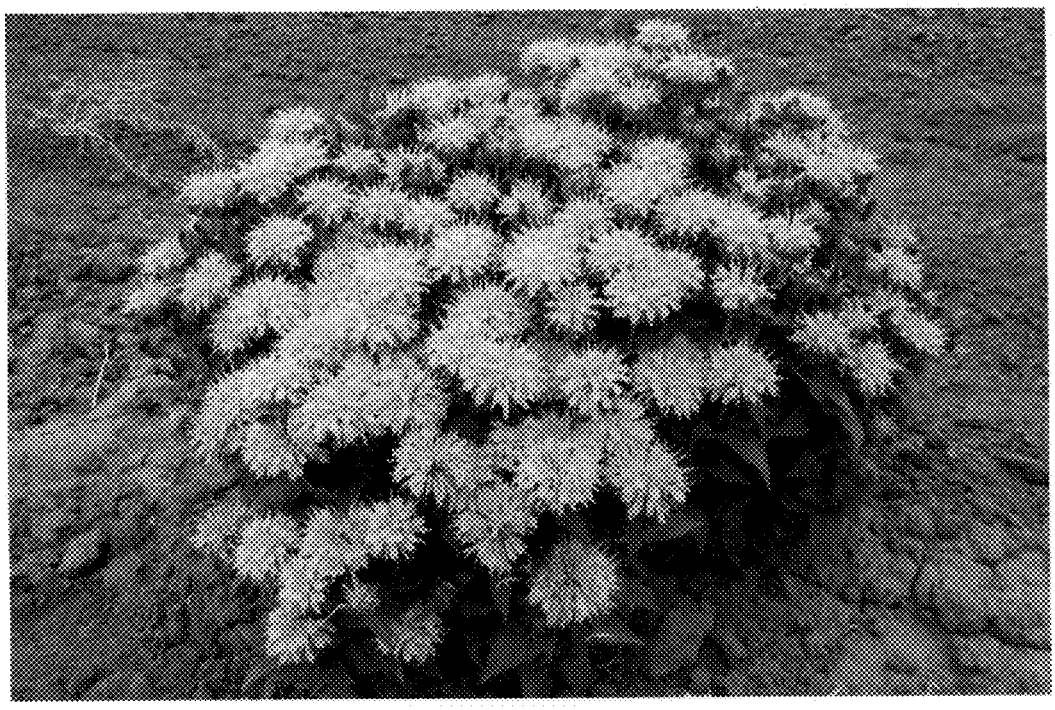
FIG. 1 provides a view of a plant of 'MCmum' in bloom.
Figure 2:
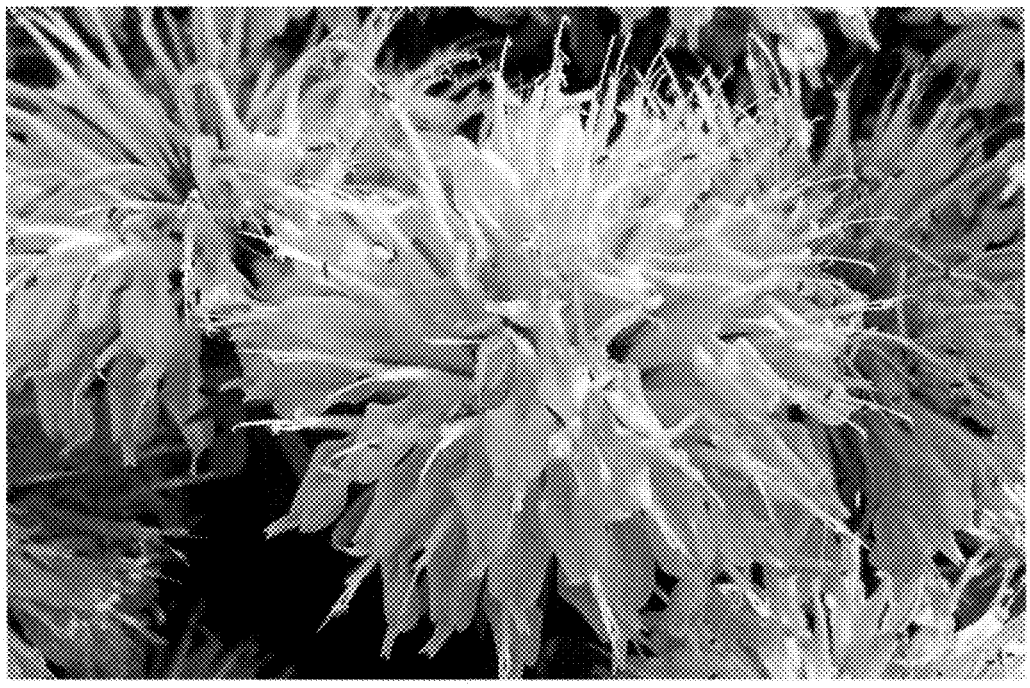
FIG. 2 provides a close-up view of an inflorescence of 'MCmum'.

The colors in the photographs are as close as possible with the digital photography and printing techniques utilized and the color codes in the detailed botanical description accurately describe the new *Monarda.*

DETAILED BOTANICAL DESCRIPTION

The detailed botanical data was collected on plants about one year in age as grown in one-gallon containers in St. Paul, Minn. with the mature height and spread, disease resistance and cold hardiness describing plants that were field grown for three years in Morden, Manitoba, Canada and St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Botanical classification.*—*Monarda didyma* 'MCmum'.

*Parentage.*—Proprietary, unnamed selections of *Monarda didyma* produced by open pollination.

*Blooming habit.*—Abundantly from July to early September, can be prolonged and more dense with deadheading and pruning.

*Plant habit.*—Mid-sized, compact and mounded.

*Height and spread.*—Mature plants reach about 50 to 60 cm in height and 50 cm in width.

*Cold hardiness.*—U.S.D.A. Zones 3 to 8.

*Diseases and pests.*—Resistance to powdery mildew (*Sphaerotheca pannosa* var. *rosa*), no insect problems observed.

*Propagation.*—Softwood stem cuttings or division.

*Growth.*—Vigorous and strong.

*Root.*—Fleshy roots (about 164C in color) from stolons (N77B and N77C in color).

Branch description:

*Stem shape.*—Square.

*Stem color.*—Young; 144B, mature; a blend of 144B and N199B.

*Stem surface.*—Pubescent when young, becomes woody as they mature.

*Branching.*—An average of 7 flowering stems with an average of 4 lateral branches per main stem, new non-flowering basal stems are produced throughout the season on short stolons.

*Stem size.*—Main stems; an average of 26 cm in length and 4.5 mm in width, lateral branches; an average of 10 cm in length and 3 mm in width, arranged opposite on upper portion of stem with an internode length an average of 2 cm.

Foliage description:

*Leaves.*—Opposite arrangement, ovate to ovate-lanceolate in shape, rounded to slightly cordate base, acuminate apex, serrulate margins, dull, puberulent and glandular on upper surface and lower surface with short hairs on veins on lower surface and on margins, an average of 5 cm in length and 2.2 cm in width, mint fragrance if crushed, color of young foliage upper surface; 144A, color of young foliage lower surface; color between 144A and 144B, color mature foliage upper surface; 137A, color mature foliage lower surface; a color between 138A and 138B, venation; pinnate, non conspicuous, 138B in color on upper and lower surface.

*Petioles.*—Average of 8 mm in length and 2 mm in diameter, slightly sulcate in shape, 138B in color on upper and lower surface, pubescent surface.

Inflorescence description:

*Inflorescence type.*—Borne terminally in whorls or as verticillaster.

*Inflorescence number.*—1 per lateral stem.

*Inflorescence fragrance.*—Pungent mint.

*Inflorescence size.*—Average of 2.5 cm in depth and 4.5 cm in diameter.

*Peduncles.*—Square in shape, an average of 1.8 cm in length and 4 mm in diameter, surface is pubescent, color is a blend of 144A and 144B.

*Bracts.*—About three rows per verticillaster, outer bracts (one row); an average of 4 cm in length and 1.8 cm in width, broadly lanceolate in shape, surface is dull and puberulent on upper and lower surface, margin serrated, truncate base on short petiole about 6 mm in length and 4 mm in width and 144B in color, narrowly acute apex, color of upper surface is 137A with veins 144b in color, color of lower surface is 138A with veins 138C, inner bracts (about 2 rows); an average of 1.8 cm in length and 2.5 mm in width, lanceolate in shape, truncate base, attenuate apex, puberulent surface, 144B in color on upper and lower surface.

*Flower number.*—An average of 40 per inflorescence.

*Flower buds.*—Elongated tube in shape, average of 1 cm in length and 2 mm in width, 64B in color with base with calyx portion 138B, surface is glabrous.

*Flower longevity.*—About 5 to 7 days, depending on temperature.

*Flower type.*—Tubular.

*Flower size.*—Average of 1.2 mm in diameter and 3 cm in depth.

*Calyx.*—Campanulate in form, an average of 6 mm in length and 2 mm in width, comprised of fused sepals, 5-pointed.

*Sepals.*—5, fused with very tip free, margins and base are fused, apex of tips attenuate, color of outer and inner surface 144B with apex 144A and base 144C, upper surface and lower surface is puberulent and ridged with stiff short hairs near apex, average of 6 mm in length with triangular tips about 1 mm in length and width.

*Petals.*—2, fused to tube about 1 cm in length and 3 mm in width, the upper lip; hooded, erect, and lanceolate in shape, about 2 cm in length with free portion 1 cm in length and 2 mm in width, apex attenuate, margin entire and wavy, lower lip; free portion is spreading and heart-shaped with linear notched lobe at apex about 3 mm in length and 1.5 mm in width, margin entire a wavy with notched lobe at apex, color of opening and mature flowers outer surface; a blend of 65A and 65C, color of opening flowers inner surface; a blend of 65A and N65C, color of mature flowers inner surface; a 64A with margins of lower lips 64D, surface is puberulent.

*Pistil.*—1, stigma is an average of 5 mm in length and N74D in color, style is an average of 2.2 cm in length and N155B in color and translucent, ovary is about linear and about 3 mm in length and N155B in color.

*Stamens.*—2, filaments are about 1 cm in length and N155B in color, anthers are an average of 1.5 mm in length, N199D in color, pollen is moderate in abundance and 13C in color.

*Seeds.*—1 per flower, average of 1.4 mm in length and 0.8 mm in width, oval to rice shaped, color is 199B.

It is claimed:

1. A new and distinct cultivar of *Monarda* plant named 'MCmum' as herein illustrated and described.

* * * * *